United States Patent
Propp et al.

(10) Patent No.: US 7,351,248 B2
(45) Date of Patent: Apr. 1, 2008

(54) SURGICAL INSTRUMENT WITH SNAG FREE BOX HINGE

(75) Inventors: Donald J Propp, Dewitt, MI (US); Gary A. Gillis, Ann Arbor, MI (US)

(73) Assignee: Tri-State Hospital Supply Corporation, Howell, MI (US)

(*) Notice: Subject to any disclaimer, the term of this patent is extended or adjusted under 35 U.S.C. 154(b) by 869 days.

(21) Appl. No.: 10/284,519

(22) Filed: Oct. 30, 2002

(65) Prior Publication Data

US 2003/0181944 A1    Sep. 25, 2003

Related U.S. Application Data

(60) Provisional application No. 60/367,610, filed on Mar. 25, 2002.

(51) Int. Cl.
*A61B 17/28* (2006.01)
(52) U.S. Cl. .................................. 606/205; 81/416
(58) Field of Classification Search ............... 600/564; 604/22; 606/174, 206, 208, 210, 205, 207
See application file for complete search history.

(56) References Cited

U.S. PATENT DOCUMENTS

| 2,726,657 | A |   | 12/1955 | Tabrah |          |
|-----------|---|---|---------|--------|----------|
| 3,503,398 | A | * | 3/1970  | Raible et al. | 606/207 |
| 3,763,726 | A | * | 10/1973 | Hildebrand | 81/416 |
| 4,803,983 | A | * | 2/1989  | Siegel | 606/151 |
| 4,821,719 | A | * | 4/1989  | Fogarty | 606/158 |
| 5,624,454 | A | * | 4/1997  | Palti et al. | 606/151 |
| 6,733,508 | B1 | * | 5/2004 | Propp et al. | 606/120 |

FOREIGN PATENT DOCUMENTS

| DE | 23 64 287   | 6/1975  |
|----|-------------|---------|
| DE | 201 13 018  | 11/2001 |

* cited by examiner

*Primary Examiner*—Julian W. Woo
*Assistant Examiner*—Victor Nguyen
(74) *Attorney, Agent, or Firm*—Fildes & Outland, P.C.

(57) ABSTRACT

A surgical instrument includes a pair of elongated members joined together by a box hinge. The box hinge is formed of a slot in the first member having substantially flat, generally parallel sides and a hinge portion in the second member. The hinge portion of the second member conforms to the generally flat surfaces of the slot and is generally the same width as that of the second member on either side of the box hinge. The width of the first elongated member is larger than the width of the second elongated member at either end of the box hinge portion. The transitional slope of the side surfaces of the second elongated member is nearly flat between the box hinge portion, the handle end portion, and the working tip portion. The unique construction of the box hinge creates a snag-free surface that allows for the use of the instrument for tasks such as suturing without the suturing thread snagging on the instrument.

10 Claims, 3 Drawing Sheets

FIG - 1
PRIOR ART
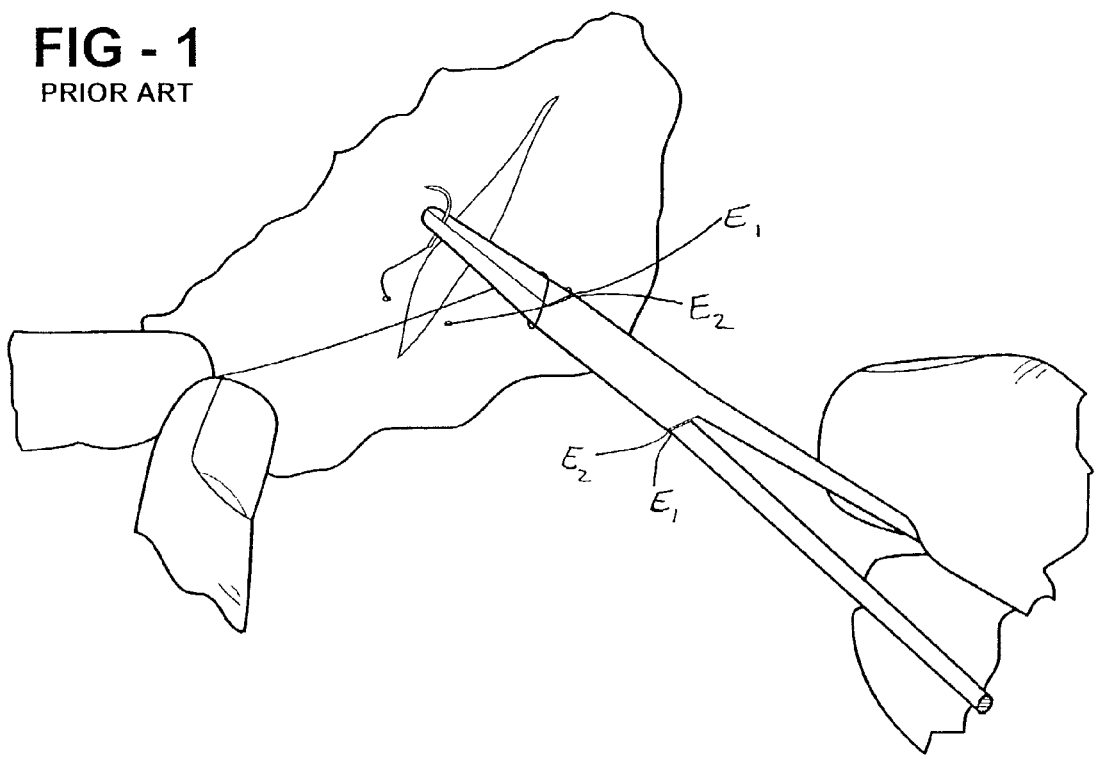
FIG - 2
PRIOR ART
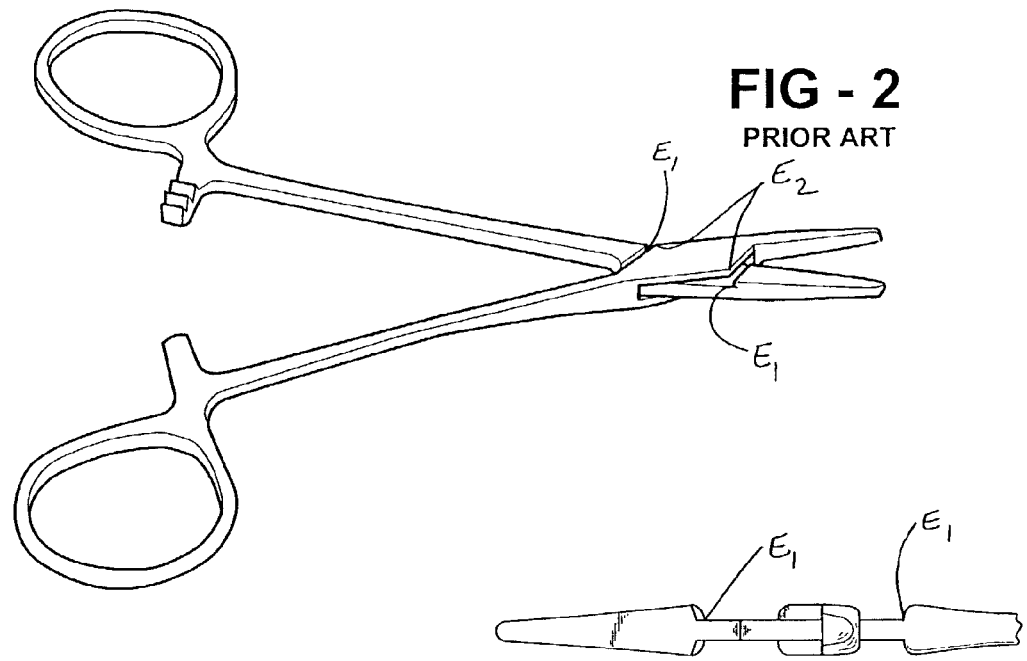
FIG - 3
PRIOR ART

SURGICAL INSTRUMENT WITH SNAG FREE BOX HINGE

CROSS REFERENCE TO RELATED APPLICATION

This application claims the benefit of U.S. Provisional Application No. 60/367,610, filed Mar. 25, 2002.

TECHNICAL FIELD

This invention relates to medical and surgical instruments and more particularly to surgical instruments such as needle holders, forceps, hemostats, clamps, and occluders which incorporate a precision box hinge.

BACKGROUND OF THE INVENTION

Medical and surgical instruments such as needle holders, needle drivers, forceps and occluders that incorporate a box hinge between handle ends and working tip ends are well known. Referring to FIGS. 1 through 3, these instruments include a pair of members joined together by a box hinge. Forming the box hinge one of the members includes a slot having flat, parallel sides and the other member includes a portion machined to conform with the flat, parallel sides of the slot. The machined portion extends through the slot in an assembled instrument. A hinge pin extends through the parallel sides of the slot and through the machined portion of the other member disposed in the slot. It is known that suture thread does snag at or on edges $E_1$ around the machined portion of the one member and around or under machined edges $E_2$ machined around the slot. In an attempt to reduce snags some manufacturers bevel the machined edges, or attempt to provide very expensive and precise matched grinding of the handles at either end of the box hinge where the machined portion first interfaces with the slot.

Even with the beveled edges a suture may snag above and below the pivot point of the hinge as a surgeon is tying a knot in the suture, or when a prior art instrument goes into and out of an array of temporarily placed suture threads placed in, or around, a large wound or opening in tissues; in which one or more layers is held open by multiple instruments and suture threads. Such snagging can occur when preparatory knot loops, or partial turns, are moving either up, or down, the instrument body, and at locations both above, and below, the box hinge. Snagging potential increases directly with smaller suture thread and with larger suture needles (more open jaws and mismatch at the prime snag areas). Likewise, the matched grinding has the disadvantage of being costly typically still snagging when suture thread is of very fine diameter, and still leads to snagging due to mismatch of the interface as the working tip ends are opened slightly to hold the suture needle or other objects.

SUMMARY OF THE INVENTION

The present invention provides a box hinge for a medical or surgical instrument that completely eliminates any possibility of snagging a suture on edges of the instrument around the box hinge.

Accordingly, interacting surfaces of a snag-free medical or surgical instrument box hinge includes edges having a smooth cooperative transition so that relative movement between the instrument box hinge and a suture is uninterrupted as there are no snag points along edges of the box hinge for the suture to get caught in or on during working movement.

More specifically, a surgical instrument in accordance with the invention includes a pair of elongated members joined together by a box hinge. The box hinge is formed by a slot in the first member having substantially flat, generally parallel sides and, instead of a machined portion, as in the known art, a hinge portion of generally continuous section in the second member. The hinge portion of the second member conforms and cooperates with the substantially flat surfaces of the slot. The hinge portion of the second member may be generally the same width as that of the second member on either side of the box hinge, thereby eliminating points where a suture can snag above and below the box hinge. In other words, the hinge portion of the second member preferably has a generally continuous cross sectional shape being generally that of portions of the second member on either end of the hinge portion.

In an embodiment of the invention the instrument includes two elongated members, each of which comprises a box hinge portion, a handle end portion and a working tip portion. The length of the handle end portion is generally longer than the length of the working tip portion. The handle end portion comprises a circular finger handle and a locking mechanism that holds the box hinge in a closed position. The working tip portion may have working surfaces that include a plurality of ridges, or various other kinds of grasping structure, shapes, and designs. The box hinge comprises a slot in the box hinge portion of the first elongated member and the box hinge portion of the second elongated member received in the slot. The box hinge portion of the second elongated member conforms to the generally flat surfaces of the slot. The width of the first elongated member is larger than the width of the second elongated member at either end of the box hinge portion. In this embodiment, the outside overall width of the first elongated member including the slot may also be slightly wider relative to conventional instruments. The slope of the side surfaces of the second elongated member is nearly flat, although there may be some tapering of the member between the box hinge portion and the handle end portion on one end of the box hinge and the box hinge portion and the working tip portion on the other end of the box hinge.

Alternatively, the hinge portion may be formed by machining the hinge portion without any step between handle end or tip end and box hinge portion to provide no snag inducing surfaces for a suture to catch on.

External edges of the first elongated member that includes the slot may be tapered or curved toward ends above and below the pivot point so as not to create any snag points.

A health care professional can use medical or surgical instruments that incorporate a snag-free box hinge through methods that do not have to compensate for snagging sutures.

These and other features and advantages of the invention will be more fully understood from the following detailed description of the invention taken together with the accompanying drawings.

BRIEF DESCRIPTION OF THE DRAWINGS

In the drawings:

FIG. 1 is a perspective view of a prior art surgical instrument including a box hinge comprised of two hinged members, one having a slot with parallel sides and the other having a stepped down portion machined to fit within the parallel sides in a closed suture needle holding position, illustrating a suture being snagged on edges of the stepped down portion and other edges;

FIG. 2 is a perspective view of the prior art surgical instrument of FIG. 1 showing the edges in the member where snagging occurs;

FIG. 3 is an end view of the prior art surgical instrument of FIG. 2 wherein the working tip portions are open and spaced and illustrating steps in the hinged members around the box hinge portion;

DETAILED DESCRIPTION OF THE INVENTION

Figure 4:
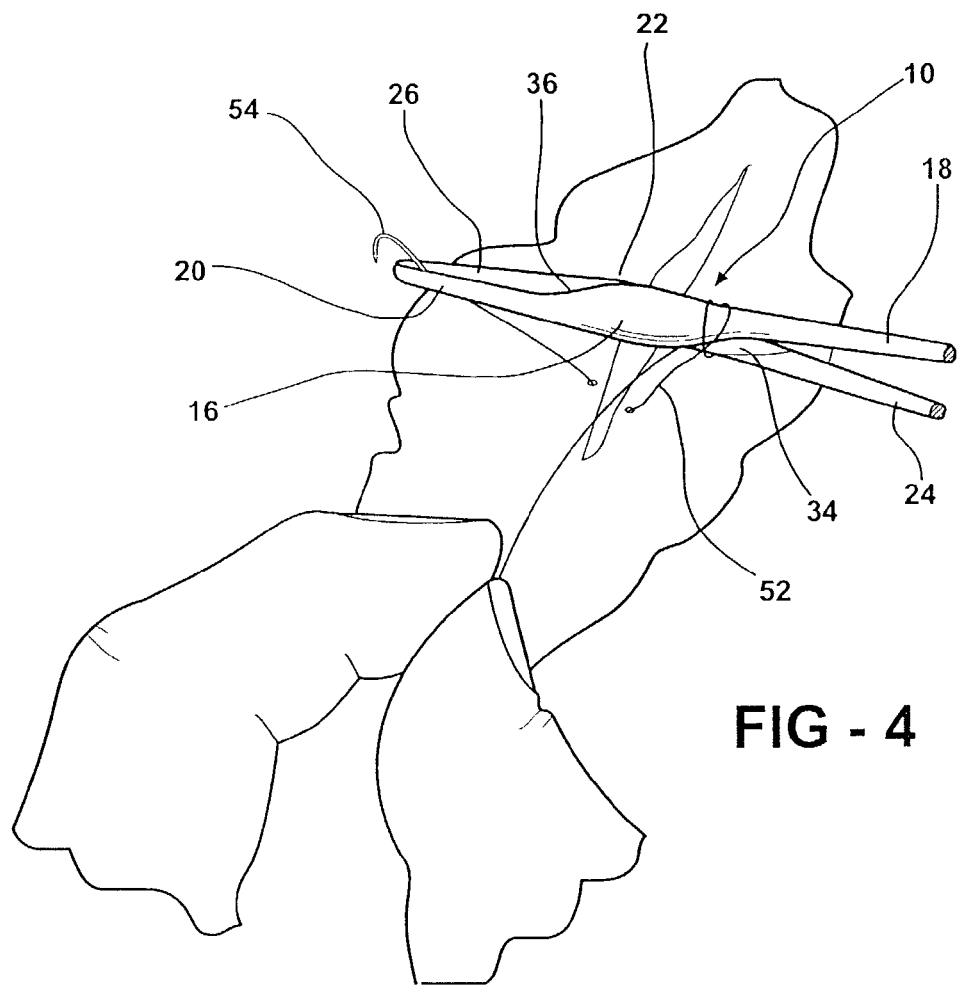
FIG. 4 is a perspective view of a surgical instrument including a snag free box hinge in accordance with the invention in an operative position mounting a suturing needle illustrating a surgeon's knot and an absence of edges on which the suture could snag.
Figure 5:
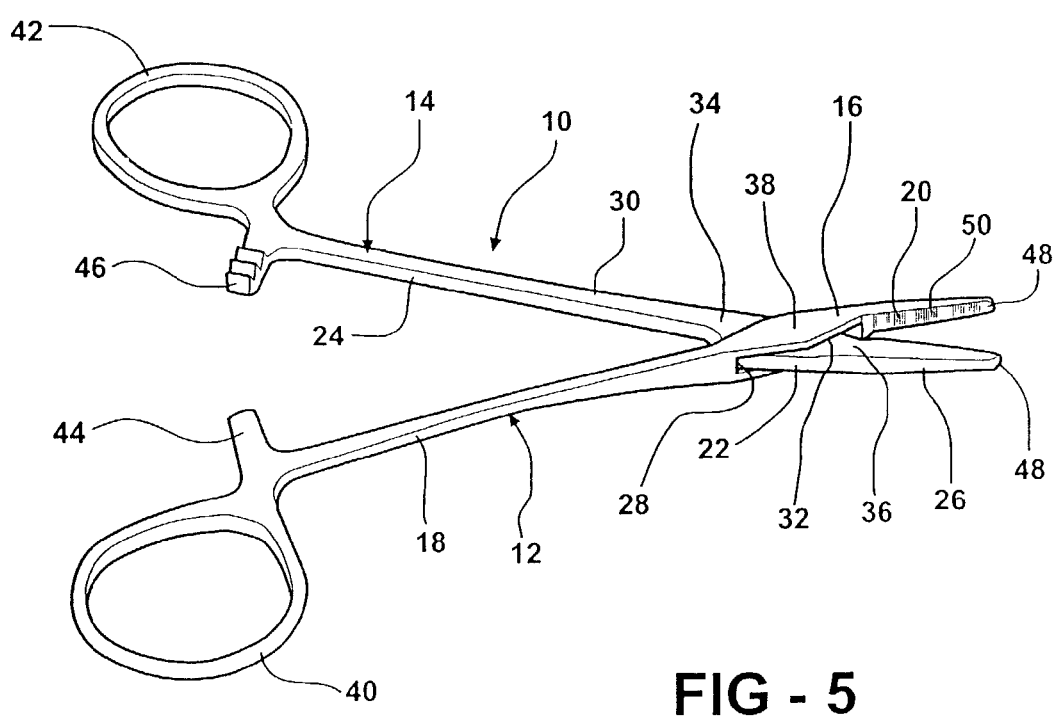
FIG. 5 is a perspective view of the surgical instrument of FIG. 4 illustrating a box hinge including two members, one having a slot with parallel sides and the other having a smooth, step-free portion.
Figure 6:
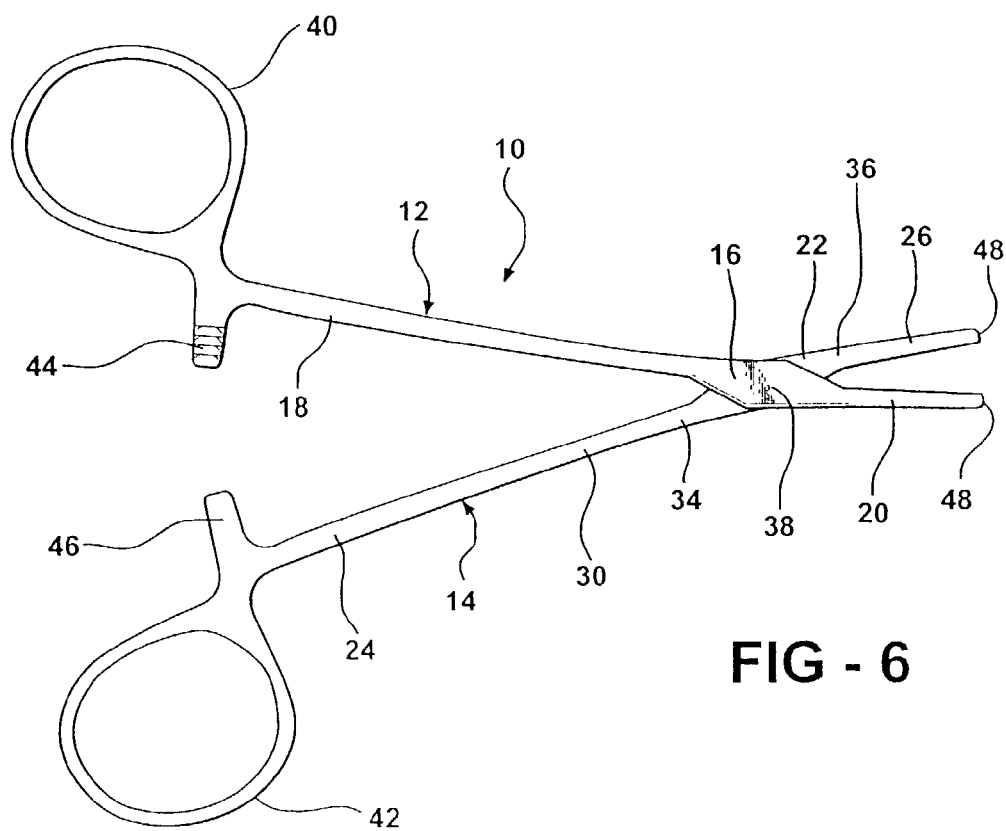
FIG. 6 is a plan view of the surgical instrument of FIG. 4 in the open position.
Figure 7:
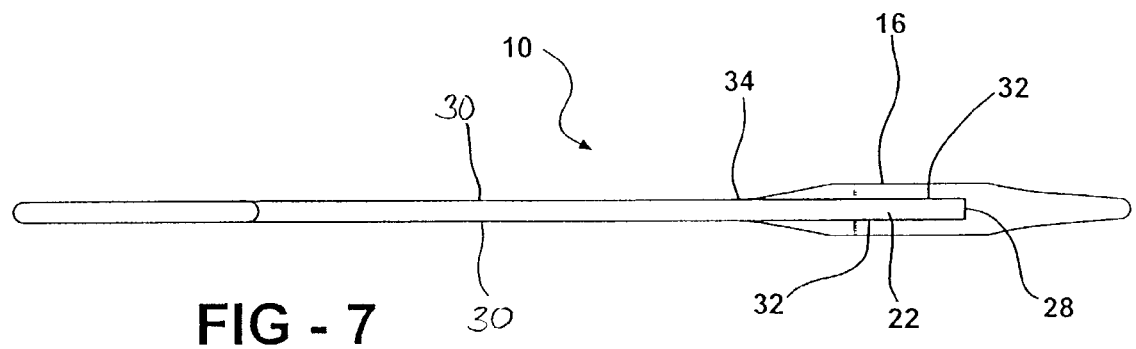
FIG. 7 is a side view of the surgical instrument of FIG. 4 in the open position.
Figure 8:
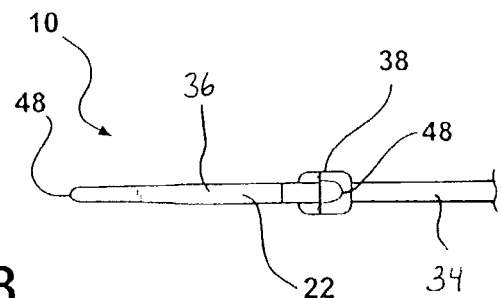
FIG. 8 is an end view of the surgical instrument including a snag free box hinge of FIG. 6 wherein the working tip portions are open and spaced and illustrating the absence of any step in the hinged members around the box hinge portion.

Referring now to FIGS. 4 through 8 of the drawings in detail, numeral 10 generally indicates a surgical instrument in accordance with a first embodiment of the present invention. As is more fully hereinafter described, the surgical instrument 10 provides for snag free movement of a suture along the box hinge portion of the surgical instrument.

As illustrated in FIGS. 4 through 8, a surgical instrument 10 includes a first elongated member 12 and a second elongated member 14. The first elongated member 12 includes a first box hinge portion 16, a handle end portion 18 and a working tip portion 20. The second elongated member 14 includes a second box hinge portion 22, a handle end portion 24 and a working tip portion 26. The second box hinge portion 22 has opposing side surfaces 30 that span the length of the second elongated member 14.

The first box hinge portion 16 includes a slot 28 that has generally flat parallel sides 32 for receiving the second box hinge portion 22 therein. The second box hinge portion 22 has a cross section conforming to the generally flat parallel sides 32 of the slot 28. The second box hinge portion 22 illustrated is also generally the same width as the handle end portion 24 and the working tip portion 26 on either end 34, 36 of the box hinge portion 22 such that the slope of the side surfaces 30 of the second elongated member 14 from the handle end portion 24 through the second box hinge portion 22 to the working tip portion 26 is nearly flat, having a continuous, non-stepped, cross sectional shape. The result is that there are no steps on either end of the box hinge on which to snag a suture. This is in contrast to the machined portion of the prior art which results in steps $E_1$ and $E_2$. A hinge pin 38 extends through the parallel sides of the slot 28 and through the second box hinge portion 22 connecting the first elongated member 12 to the second elongated member 14.

Alternatively, the second box hinge portion 22 can be disposed between handle end 24 and working tip 26 portions that therein provide a long smooth oblique transition, therby being generally nearly flat and extending outward and away from the box hinge portion toward the handle end portion on one end of the box hinge and the working tip portion on the other end of the box hinge.

The handle end portions 18, 24, include a circular handle 40, 42 and a cooperating locking mechanism 44, 46 disposed near the circular handles 40, 42 that are interconnectable to effectively lock the distal tip portions 20, 26 of the first and second elongated members 12, 14 in urged engagement. The inner working surfaces 48 of the working tip portions 20, 26 may include a plurality of ridges, or other grasping structures, 50 that enhance the grip of the working tips when the surgical instrument 10 is in the operative position, as seen in FIG. 4.

In FIG. 4, an advantage of the surgical instrument 10 is shown. The surgical instrument 10 is in the operative position clamping a surgical suturing needle between the working tip portions 20, 26. suture 52 attached to a needle 54 engaged between the working tips 20, 26 does not snag on the members at the ends 34, 36 between the box hinge portion 16, 22 portions 20, 26 respectively when the suture is in contact with the surgical instrument 10, such as when a surgeon is tying a knot in the thread, or the instrument 10 is moving relative to and in contact with other suture threads disposed about an open wound.

The box hinge structure herein described can also be applied to numerous other types of non-needle holder surgical instruments, such as any manual surgical instrument, clamp type forceps, blood vessel clamp, and scissors that employ a box hinge. These instruments can be formed of stamped metal construction and can be readily disposable, or reusable, at manufacturer's and users option.

As an example of a suture needle holder application, a medical care provider uses the surgical instrument together with a suturing needle and suture thread to conduct suturing in a which a surgical instrument according to the invention is provided, a suture needle with suture thread is operatively mounted in the working tip portion of the instrument, and a wound or other opening in a patient is sutured in accordance with common medical practice.

although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed:

1. A surgical instrument comprising:
a first elongated member having a handle end portion, a working tip portion and a box hinge portion between said handle and tip end portions;
a second elongated member having a handle end portion, a working tip portion and a box hinge portion between said handle and tip end portions;
said first box hinge portion being defined by a slot having generally flat parallel sides for receiving said second box hinge portion therein;
said second box hinge portion having a continuous, non-stepped, cross-sectional shape conforming with the flat, parallel sides of the slot in said first box hinge portion and comprising a surface generally perpendicular to the parallel sides, the surface having a width that is generally continuous in width with the handle and tip portions of the second elongated member on either side of the second box hinge portion; and a hinge pin extending through the parallel sides of the slot and through said second box hinge portion hingedly connecting together said first and second elongated members.

2. The surgical instrument of claim 1, wherein the side surfaces of the second elongated member have a nearly flat transitional slope therebetween the box hinge portion and the handle end portion on one end and the box hinge portion and the working tip portion on the other end.

3. The surgical instrument of claim 1, wherein the transitional slope of the second elongated member between the box hinge portion and the handle end portion on one end and the box hinge portion and the working tip portion on the other end is a long smooth oblique transition.

4. The surgical instrument of claim 1, wherein the external edges of the box hinge portion of the first elongated member are curved toward ends above and below the pivot point of the hinge.

5. The surgical instrument of claim 4, wherein said curved external edges have smooth cooperative transitions for a distance defined by the length equal to or less than the slot length.

6. The surgical instrument of claim 1, wherein the first elongated member is wider than the second elongated member at either end of the box hinge portion.

7. The surgical instrument of claim 1, wherein the handle end portion includes a circular handle and a locking mechanism interconnected at the far end of the handle end portion.

8. The surgical instrument of claim 1, wherein the inside surface of the working tip portion includes a gripping structure.

9. The surgical instrument of claim 1, wherein the length of the handle end portion is generally longer than the length of the working tip portion.

10. An improved surgical instrument of the type having two elongated members, each member having a working tip portion, a handle end portion, and a box hinge portion, and a hinge pin, wherein the improvement comprises a box hinge defined by a slot located in the box hinge portion of the first elongated member having flat parallel sides for receiving the box hinge portion of the second elongated member therein, the ends of the second box hinge portion having a width narrower than the width of the ends of the first box hinge portion and a continuous, non-stepped, cross-sectional shape, and the hinge pin hingedly connecting the first and second elongated members, such that the side edges of first elongated member are larger relative to the side edges of the second elongated member at either end of the box hinge; wherein the cross sectional shape comprises a surface generally perpendicular to the parallel sides, the surface including a width that is generally continuous in width with the working tip portion and the handle end portion.

* * * * *

US007351248C1

(12) EX PARTE REEXAMINATION CERTIFICATE (9114th)
United States Patent
Propp et al.

(10) Number: US 7,351,248 C1
(45) Certificate Issued: Jul. 3, 2012

(54) SURGICAL INSTRUMENT WITH SNAG FREE BOX HINGE

(75) Inventors: Donald J Propp, Dewitt, MI (US); Gary A. Gillis, Ann Arbor, MI (US)

(73) Assignee: Centurion Medical Products Corporation, Williamston, MI (US)

Reexamination Request:
No. 90/009,638, Dec. 16, 2009

Reexamination Certificate for:
Patent No.: 7,351,248
Issued: Apr. 1, 2008
Appl. No.: 10/284,519
Filed: Oct. 30, 2002

Related U.S. Application Data

(60) Provisional application No. 60/367,610, filed on Mar. 25, 2002.

(51) Int. Cl.
*A61B 17/28* (2006.01)

(52) U.S. Cl. .......................................... 606/205; 81/416
(58) Field of Classification Search .................... None
See application file for complete search history.

(56) References Cited

To view the complete listing of prior art documents cited during the proceeding for Reexamination Control Number 90/009,638, please refer to the USPTO's public Patent Application Information Retrieval (PAIR) system under the Display References tab.

*Primary Examiner* — Jeanne M Clark

(57) ABSTRACT

A surgical instrument includes a pair of elongated members joined together by a box hinge. The box hinge is formed of a slot in the first member having substantially flat, generally parallel sides and a hinge portion in the second member. The hinge portion of the second member conforms to the generally flat surfaces of the slot and is generally the same width as that of the second member on either side of the box hinge. The width of the first elongated member is larger than the width of the second elongated member at either end of the box hinge portion. The transitional slope of the side surfaces of the second elongated member is nearly flat between the box hinge portion, the handle end portion, and the working tip portion. The unique construction of the box hinge creates a snag-free surface that allows for the use of the instrument for tasks such as suturing without the suturing thread snagging on the instrument.

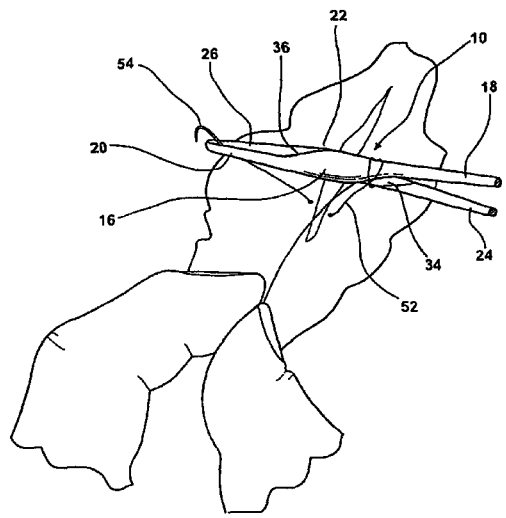

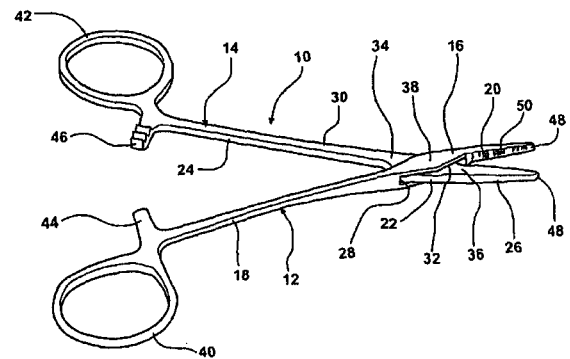

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-10 are cancelled.

* * * * *